United States Patent [19]
Collette

[11] Patent Number: 5,743,909
[45] Date of Patent: Apr. 28, 1998

[54] RADIOLOGICAL METHOD FOR PREOPERATIVE DETERMINATION OF ISOMETRIC ATTACHMENT POINTS OF AN ACL GRAFT, SURGICAL AIMING INSTRUMENT AND METHOD OF USE

[76] Inventor: Michel Collette, Avenue des 14 Bonniers 28, B-1325 Dion-Valmont, Belgium

[21] Appl. No.: 668,832

[22] Filed: Jun. 24, 1996

[51] Int. Cl.⁶ .................................................. A61B 17/17
[52] U.S. Cl. .................. 606/88; 606/86; 606/96; 606/98; 606/87
[58] Field of Search ................... 606/86, 87, 88, 606/89, 96, 97, 98

[56] References Cited

U.S. PATENT DOCUMENTS 4,708,139  11/1987  Dunbar, IV .
5,112,337  5/1992  Paulos et al. ............................ 606/98
5,570,706  11/1996  Howell ..................................... 606/88

FOREIGN PATENT DOCUMENTS 0 162 027  11/1985  European Pat. Off. .
0 440 991 A1  8/1991  European Pat. Off. .
PCT/GB93/01288  1/1994  WIPO .

*Primary Examiner*—Michael Buiz
*Assistant Examiner*—Daphna Shai
*Attorney, Agent, or Firm*—Marshall, O'Toole, Gerstein, Murray & Borun

[57] ABSTRACT

A surgical aiming instrument for a lining and guiding a piercing tool used to make a tunnel through a tibia which intersects two predefined points of the knee joint includes at its distal end a tip to be temporarily inserted in the bone. The instrument further includes means for positioning the instrument relative to the second of the predefined points. A second hollow member in line with the first member and defining therewith an axis X—X is also provided. The instrument further includes a flat arm connecting the first and second members as well as a handle. The tip is on the axis of the second member. A method of preoperative determination of isomeric attachment points includes the steps of taking two x-rays of the knee, one in an extended position and one at 90° of flexion, superimposing the x-rays, and marking various points and lines thereon from which the isomeric attachment points may be determined.

5 Claims, 5 Drawing Sheets

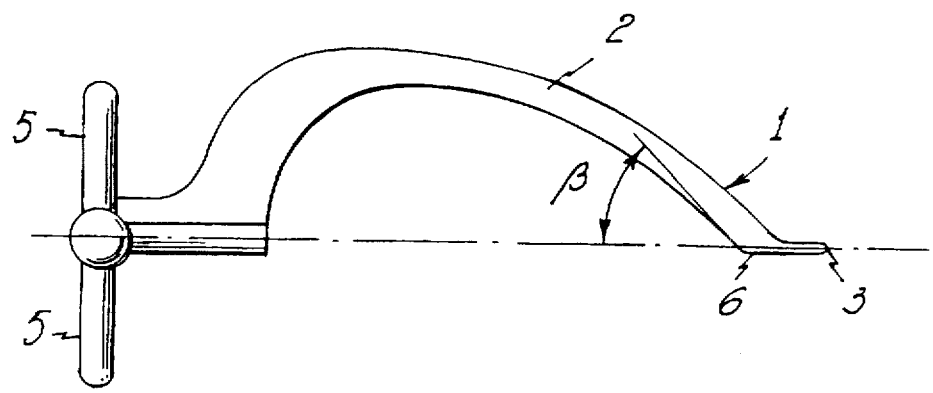
FIG. 1
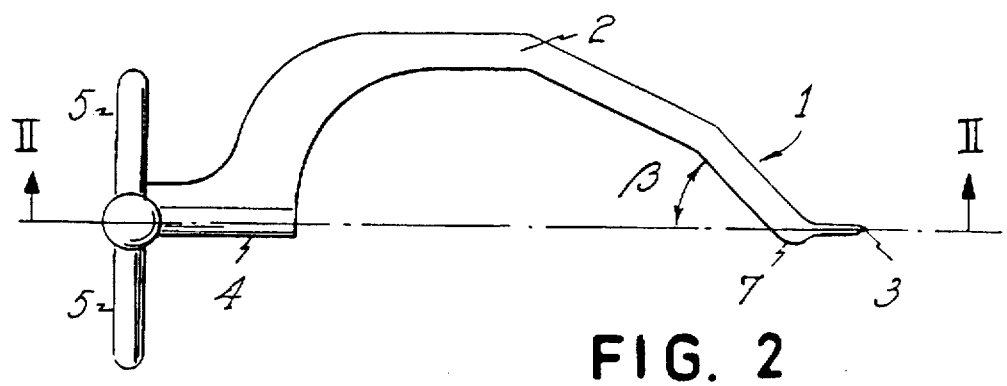
FIG. 2
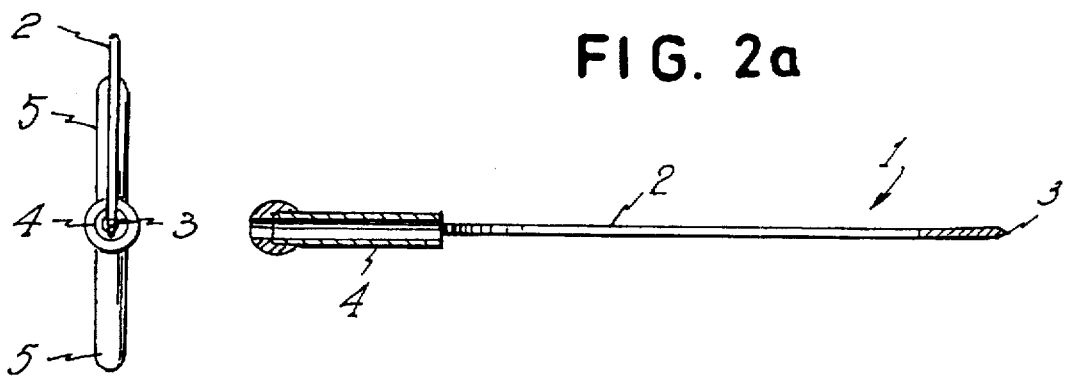
FIG. 2a
FIG. 3

RADIOLOGICAL METHOD FOR PREOPERATIVE DETERMINATION OF ISOMETRIC ATTACHMENT POINTS OF AN ACL GRAFT, SURGICAL AIMING INSTRUMENT AND METHOD OF USE

BACKGROUND AND SUMMARY OF THE INVENTION

The present invention relates to a radiological method for preoperative determination of isometric attachment points of an anterior cruciate ligament (ACL) graft, a surgical aiming instrument to reach these points, and a method of use of the instrument.

More particularly, the aiming instrument is provided to align and guide a piercing member intended to pierce a tunnel through a tibia, the axis of the tunnel intersecting two points of the knee joint, namely a point on the tibial plateau and a point of the region between the femoral condyles.

In orthopedic surgery of the knee joint, in order to replace the anterior cruciate ligament, a tunnel to be used as an attachment housing for the substitute ligament has to be pierced in the tibial bone and in the femoral bone.

In view of an isometric setting of the substitute ligament, each tunnel must emerge at a predetermined point, respectively of the tibial plateau and of the intercondylian region of the femur. Methods are known for determining these points. These points can be determined by the surgeon, before the operation, for example by radiography or any other known method. (See, for example, European Patent Documents EP-B-0 162 027 and EP-A-0 408 416), or during the operation, by direct arthroscopic observation.

A problem faced by the surgeon during such an operation, is to pierce the tunnel in the tibia in such a way that it emerges at the first predetermined point of the tibial plateau, and that the axis thereof also intersects the second predetermined point of the femur.

Indeed, when these conditions are met, the tunnel in the tibia and the tunnel in the femur are perfectly in line with each other, in addition to emerging at the desired points in the joint.

This alignment is important; indeed:

in the technique of endoscopic ligamentoplastic surgery providing for the alignment of the tibial and femoral tunnels, drilling is most often initiated in the tibia, while the tibial tunnel is thereafter used to insert the drilling tools to be used to pierce the femoral tunnel; if the axis of the tibial tunnel is inadequate, it may be thereafter difficult to reach though this tunnel the femoral point from where the femoral tunnel must begin, if one uses a technique according to which the tunnels are pierced by separate aiming at the tibia and at the femur (femoral tunnel made from outside to inside), the alignment of the axis is not so essential, as far as the points of emergence of the tunnels on the tibia and on the femur are correct; however, since the graft is in most cases inserted by pulling the graft through both tunnels, a large misalignment of the tunnels may sometimes cause such pulling to be very difficult.

On the other hand, when the surgeon works according to an arthroscopic method, and pierces the tunnels starting from the tibia, their alignment is obviously obtained automatically, but they are not necessarily correctly positioned relative to the desired, predetermined isometric points.

An object of the invention is thus to provide a radiological method for preoperative determination of the isometric points and an arthroscopic aiming instrument which allows the surgeon to make with a single aiming a tibial tunnel the axis of which is correctly positioned relative to the so determined isometric tibial and femoral points.

European Patent Document EP-B-0 162 027 discloses an instrument to align and guide a drill to be used to pierce a tunnel through the tibia and the femur, comprising, at one end, a first guiding member to be inserted between the condyles of the femur and, at a second end, a second guiding member in line with the first, remaining outside the joint. Both aligned guiding members are connected by a generally L-shaped body, so as to be able to get round the side of the tibial plateau, and the first guiding member is provided with a tip to be stuck in the tibial plateau, to form a fixed point around which the instrument can pivot around a vertical axis and a horizontal axis. By design, the axis of alignment of both aligned guiding members makes with an arm of the L-shaped body a predefined angle so that, when said arm of the L is horizontal, the alignment axis, and thus the angle of penetration of the drill into the tibia is at the predefined angle. A clinometer may be provided to check the horizontality of the horizontal arm.

The first guiding member, located at the distal end of the instrument and to be inserted into the joint, has a predefined length of 31 mm, corresponding to a standard or theoretical length of the cruciate ligament. A drawback of this instrument is the bulkiness of this distal end, which requires opening of the joint (arthrotomy), with the related traumatism, and which also makes it difficult to position the instrument within the joint.

So, if the instrument positioned relative to the predetermined tibial point can slightly pivot around the longitudinal axis of its horizontal arm, or in the horizontal plane until the end thereof abuts against the condyle, it can on the contrary practically not pivot in the vertical plane because the horizontal arm then abuts against the tibial plateau. As a result, the surgeon can not—or only with great difficulty—position the instrument at an angle other than the preset angle, to take account for anatomic specificities of the patient. The surgeon is also bound by the predefined length of 31 mm, which does not take account of individual variations. The good positioning of the instrument furthermore often requires the use of a brilliance amplifier during the operation, which substantially burdens the operation.

Finally, theoretical studies show that the searched isometry rests substantially on the position of the point of insertion at the femur, where a little error has large consequences on isometry, while the same error at the point of insertion at the tibia will have little or no consequence on isometry. Now, the instrument according to European Patent Document EP-B-0 162 027 is positioned the most precisely relative to the point of insertion at the tibia (tip stuck in the tibial plateau), while the femoral point of insertion is obtained by approximation (predefined length and inclination relative to the horizontal of the distal end) therefrom, so that the risk of error is minimum at the tibia, and maximum at the femur.

An object of the invention is to provide an improved instrument, which addresses the above referenced problems.

Another object of the invention is thus to provide a surgical aiming instrument, for aligning and guiding a drill to pierce through the tibia a tunnel the axis of which intersects two predefined points of the knee joint, namely a point of the tibial plateau and a point of the region located between the condyles of the femur.

3

These and other objects of the present invention are attained by the provision of an instrument comprising at its distal end, to be inserted in the intra-articulary space, a first member provided with a tip to be temporarily stuck in the bone, to position the instrument relative to one of the predefined points, means for positioning the instrument relative to the second of the predefined points, a second hollow member, for aligning and guiding the piercing tool, in line with the first member and defining therewith the axis of the tunnel to pierce, a flat, even, angulated arm connecting the first and the second members, and a handle, which instrument is characterized in that the tip provided at the distal end of the instrument is set on the axis of the member for aligning and guiding, and defines therewith the axis of the tunnel to be pierced.

According to other features of the invention:

the positioning means comprises the terminal edge of the arm, at the junction of the arm and the tip;

the instrument includes a boss at the junction of the arm and the tip;

the handle is provided on the member for aligning and guiding, and is centered on the axis;

the axis of the handle is located in the plane of the arm.

Other aspects, characteristics and advantages of the invention will become apparent from the detailed description which follows, and the annexed drawings.

BRIEF DESCRIPTION OF THE DRAWINGS

FIGS. 1 and 2 are side views of alternative embodiments of an arthroscopic aiming instrument according to the invention.

FIG. 2a is a sectional view taken along line II—II in FIG. 2.

FIG. 3 is an end view of the embodiment of FIG. 2.

DETAILED DESCRIPTION OF THE PREFERRED EMBODIMENTS

Figure 4:
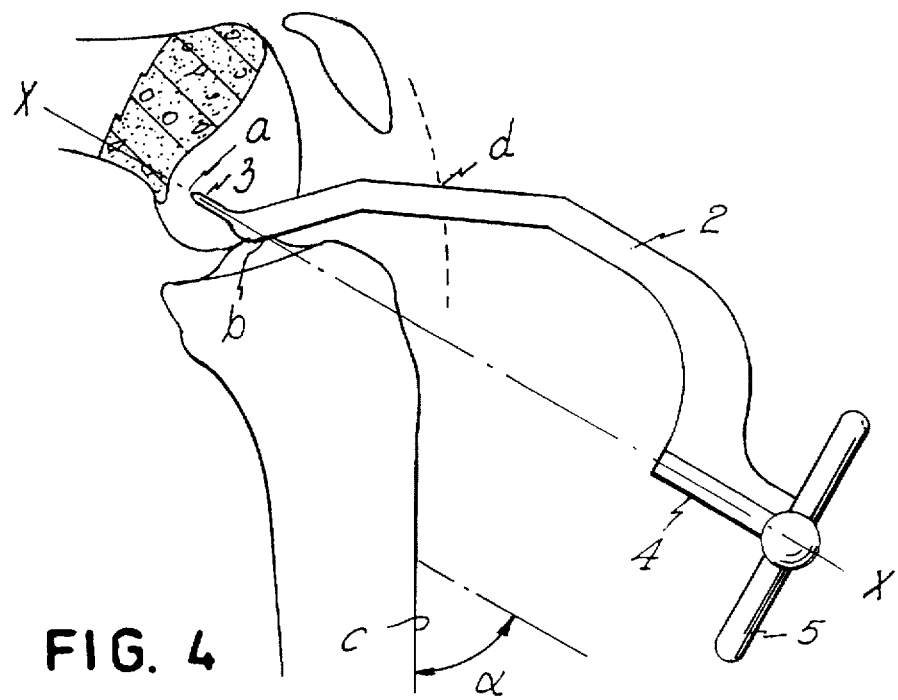
FIG. 4 is a diagrammatic side view of the instrument of the invention, positioned in the knee joint.

Turning now to the drawings, we will first describe the aiming instrument according to the invention, and thereafter the preoperative and operative methods according to the invention.

Referring more particularly to FIGS. 1 and 2, the instrument of the invention, generally designed by reference numeral 1, comprises a body made of a flat arm 2 provided with a tip 3 at a terminal part (distal end), and comprising a member 4 for aligning and guiding at its other end (proximal end).

The member 4 for aligning and guiding is hollow, and is intended to guide a pin to pierce a tunnel in the tibia. It is provided at its external periphery with projecting members 5, to be used as a handle when the instrument is handled by the surgeon.

The embodiment of FIG. 2 differs from the one of FIG. 1, on the one hand in that the arm 2 includes rectilinear, instead of including a continuous curve as in FIG. 1. On the other hand, the terminal ridge of the arm, at the junction between the tip 3 and the arm 2 is rectilinear in FIG. 1 (at 6), while it includes a boss or enlargement 7—the function of which will be explained hereafter—in FIG. 2.

The distal end of the arm 2 connects to the tip 3 at an angle $\beta$. This angle is such that, when the instrument is positioned within the joint, with the tip inclined at the predefined angle $\alpha$, the terminal part of the arm is still at least slightly apart from the tibial plateau (FIG. 4).

Although the following specific values are not to be considered as limitations, it has been noted that an angle $\beta$ from 40° to 50° was appropriate, with a preferred angle of about 46°.

An arm 2 with rectilinear portions according to FIG. 2 is preferred because the connecting regions between the rectilinear portions can serve as marks for the surgeon, regarding the depth of insertion of the instrument within the joint.

As mentioned hereabove, the attachment points of the substitute ligament, which are the ends of the tunnels, are respectively at the posterior part of the internal side of the external femoral condyle (point "a") and at the tibial plateau (point "b"), between the two protrusions of the spinal massif.

For the purpose of the ligamentoplastic surgery, the point of insertion "a" in the femur, and the point of insertion "b" in the tibial plateau, predetermined by radiography or the like, are located by means of anatomic marks, while the surgeon also determines the angle $\alpha$ formed by the projection in a vertical plane, of the X—X axis intersecting the points "a" and "b", relative to the tibial diaphysis "c". Generally speaking, this angle is included within the range of 50° to 70°.

A feature of the invention is that the tip 3 of the instrument is situated on the X—X axis passing by the center of the alignment and guiding member 4. This tip indeed allows the instrument to be very precisely positioned relative to one of the predetermined points (point a), so securing the accuracy of the aim. On the other hand, a tip at the distal end reduces the bulkiness of this end which must be inserted the deepest into the joint, and so facilitates the handling of the instrument in the joint, particularly the insertion of the instrument by a low sized vertical opening (8 to 10 mm), and the later pivoting, in the vertical plane and in the horizontal plane, of the instrument stuck at the point of insertion in the femur.

The arm 2 connecting both ends of the instrument is a flat, even arm, the medial plane of which intersects the X—X axis. An advantage of such a flat member is that it is more easily inserted in the joint, through a small cut in the articular capsule. Another advantage is that it allows an arthroscopic monitoring of the verticality of the instrument. The width of the arm is not a parameter of the invention; it will be the smallest possible, for limiting the bulkiness, while being large enough to secure the desired stiffness, taking account of its thickness, and of the kind of the material from which it is made.

The arm 2 is angulated or curved in the longitudinal direction, to allow the tip of the instrument to be inserted at the point "a" of the femur, from a short cut in the articular capsule at the antero-internal face of the knee (diagrammatically shown at "d" in FIG. 4), and by passing in the narrow space between the tibial plateau and the roof of the femoral intercondylian notch. This curve also allows the instrument to get round the tibial plateau when the instrument is pivoted in the vertical plane to bring it at the desired angle $\alpha$.

In order to bring the aiming instrument in place, the surgeon inserts the distal end 3 in the joint, through a short cut (8 to 10 mm) made at the antero-internal face of the knee, so as to stick the tip 3 at the insertion point "a" in the femur, the point "a" having preferably been predetermined by radiography or the like.

During this procedure, the surgeon monitors in a known manner the progress of the instrument by endoscopic means, and relies on anatomic marks for visually locating the predetermined "a"point.

Figure 5:
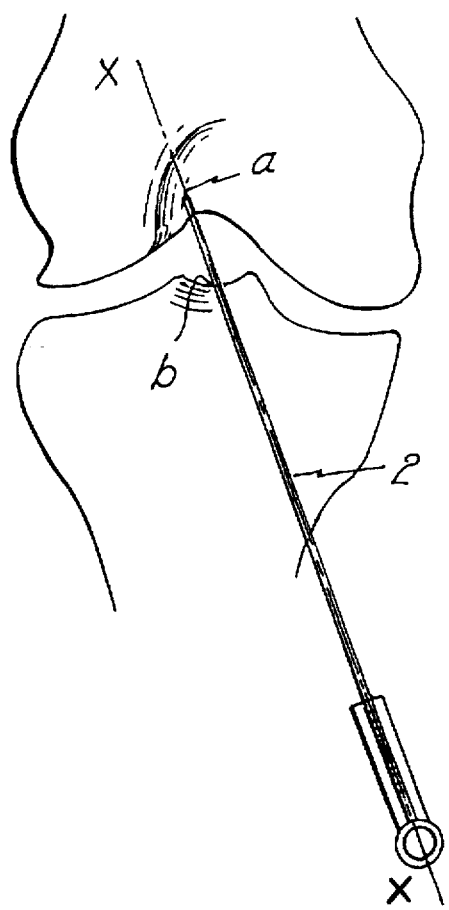
FIG. 5 is a diagrammatic front view of the instrument, in the same position as at FIG. 4.

The first point being set, it is still necessary to orient the aiming instrument so that its X—X axis intersects the point "b" of the tibia, which is located between the protrusions of the spinal massif of the tibial plateau. The aiming instrument must be pivoted, while being stuck at point "a" by the tip 3, a) on the one hand, in the frontal plane (around a vertical axis intersecting the point "a"), so that its plane (the medial plane of the arm 2) intersects the point "b" of the tibial plateau (located in the middle of the spinal massif), as seen at FIG. 5; and b) on the other hand, in the sagittal plane (around an horizontal axis passing by the point "a"), to bring the X—X axis at the predetermined α angle relative to the tibial diaphysis "c".

For the orientation procedure of the step a), the surgeon pivots the instrument to palpate the tibial plateau with the edge 6 or 7 at the junction between the arm 2 and the tip 3. So doing, and possibly with the help of anatomic marks, he can rather easily locate the cavity of the interspinal space of the tibia, the orientation of the step a) (orientation according to FIG. 5) being obtained when the edge 6 or 7 abuts against the bottom of said spinal cavity.

During this procedure, it is important that the plane of the arm be maintained substantially vertical, to avoid an angular error in the positioning of the X—X axis during step a). Indeed, the X—X axis of the instrument does not pass by the edge 6 or 7, but thereabove so that, during step a), when the surgeon palpates the middle of the spinal massif (namely the bottom of the cavity between the spinal ridges) with the edge 6 or 7, the axis lies exactly above this middle point only when the plane of the arm is vertical. In case of discrepancy between this plane and the vertical plane, an angular error will result in the positioning of the X—X axis, which is a function of the distance between the edge 6 or 7 in contact with the middle of the spinal massif, and the X—X axis.

While maintaining this orientation in the frontal plane, the surgeon must then orient the aiming instrument in the vertical or sagittal plane, according to step b) (orientation according to FIG. 4) for bringing it to the predetermined angle α. This may be done visually for a sufficiently experienced surgeon. Alternatively, the surgeon will apply on the tibial diaphysis one leg of a goniometer preset at angle α, and will then orient the X—X axis of the aiming instrument (given by the axis of the alignment member 4, or by the axis of a sharp squared tip, inserted therein in order to make a marking pre-hole) by comparison with the other leg of the goniometer.

The squared tip is thereafter replaced by a pin guide which allows a pin to be inserted through the tibia. The instrument is then withdrawn, as well as the piercing pin, and the surgeon then inserts by hand a slightly smaller pin which will serve as a guide for the cannulated drill provided for piercing the tunnel.

The tibial tunnel is later used for accessing the femoral tunnel (blind tunnel). For so doing, the surgeon introduces a pin through the tibial tunnel and into the femur at the hole made by the tip of the aiming instrument. This pin is later on used as a guide for the cannulated drill provided for piercing the femoral tunnel.

The positioning of the handle on the X—X axis facilitates the handling of the aiming instrument, particularly because the orienting movements are more instinctive, and an unintentional rotational movement of the plane of the aiming instrument around the handle produces only a rotation of the axis around itself, and not a change of orientation, as for example in the aiming instrument according to European Patent Document EP-0 162 027.

Also, a handle in the plane of the arm, as on the drawing, facilitates the handling since the surgeon so knows the position of the plane of the arm.

The length of the tip 3 is not a critical parameter of the invention. It will however be sufficient to allow to gain a firm sticking of the tip in the femur (generally with a penetration of 3 to 5 mm), while still allowing the surgeon to make the palpation step of the interspinal cavity, as mentioned hereabove. According to the invention, a tip length of 20 to 30 mm is appropriate, when measured on the X—X axis between the end of the tip and the internal edge of the arm 2.

We will hereafter describe the radiological method for preoperative determination of isometric attachment points such as the femoral point "a", and the tibial point "b" mentioned hereabove.

The isometric placement of an ACL graft remains for the surgeon both a goal to reach and an essential condition for a successful result.

Many anatomical works have been done by various authors in order to precisely determine the ideal location of the graft at the femur and, more recently, on the tibial plateau. Nevertheless, except for some recognized anatomical landmarks like the intercondylar notch roof, all of these available data remain empirical: they are collected from a small number of specimens, and yet are supposed to apply to every single knee to be treated.

I have set up a radiological method that will help the surgeon to preoperatively determine for each particular knee what should be the attachment points for an ideal graft placement, which method is described hereafter.

Figure 6A:
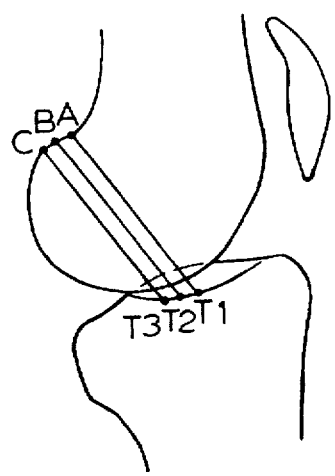
FIGS. 6a to 6e represent X-ray films of the knee to be treated, for explaining the method of determination.
Figure 6B:
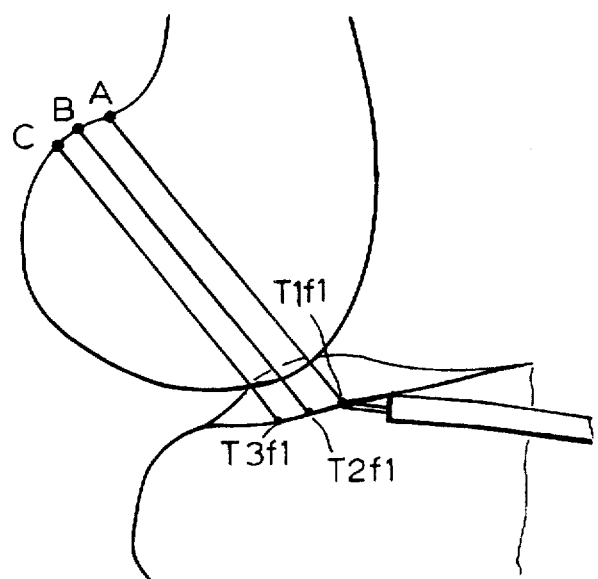
Figure 6C:
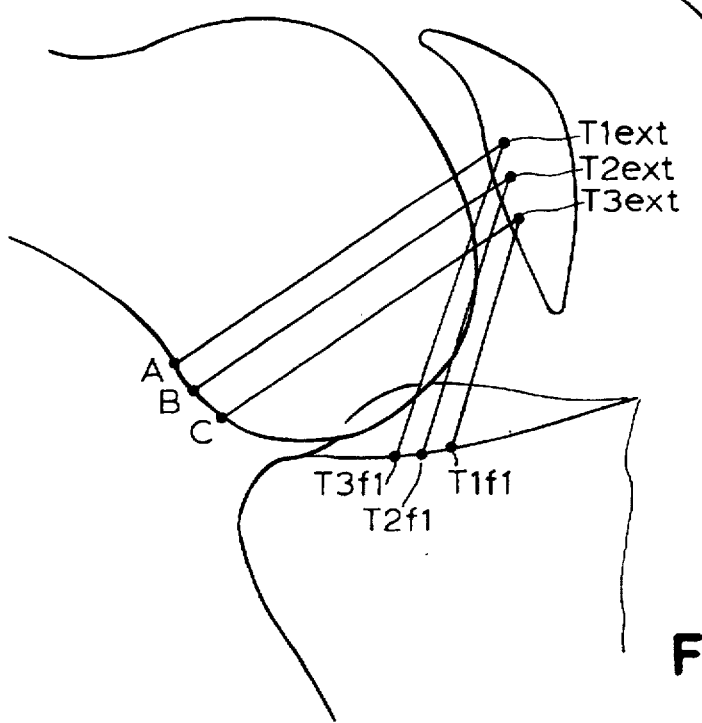
Figure 6D:
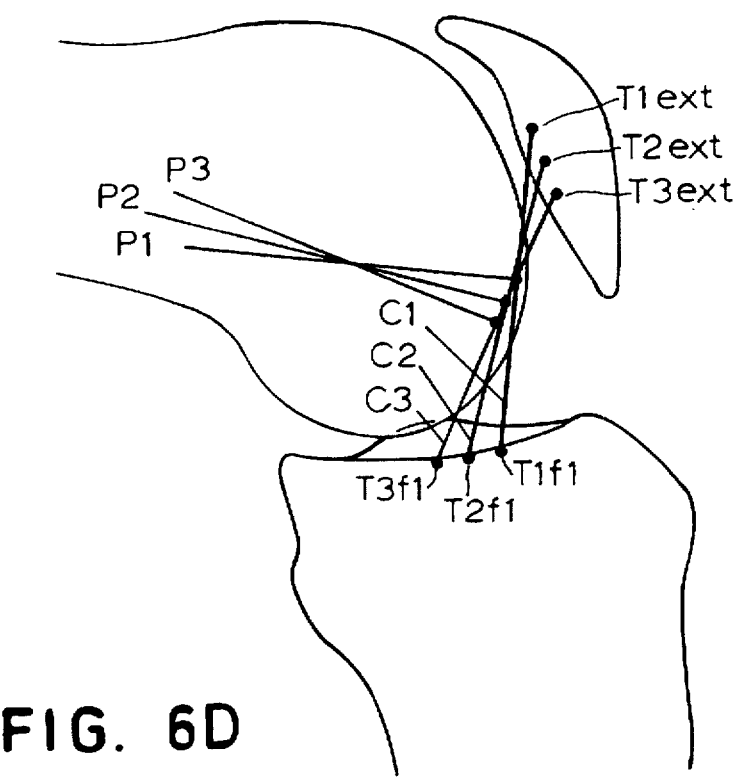
Figure 6E:
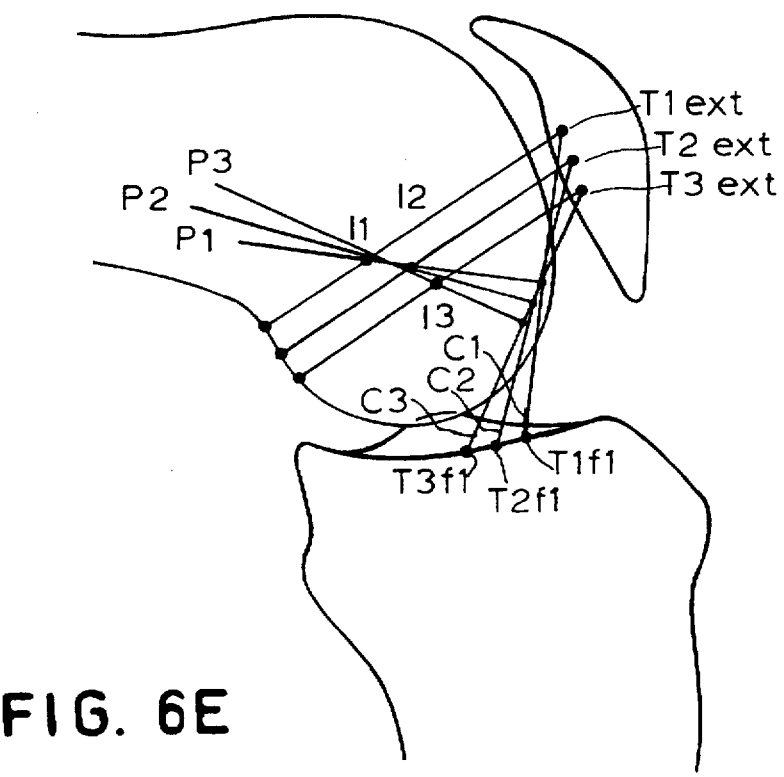
Figure 7:
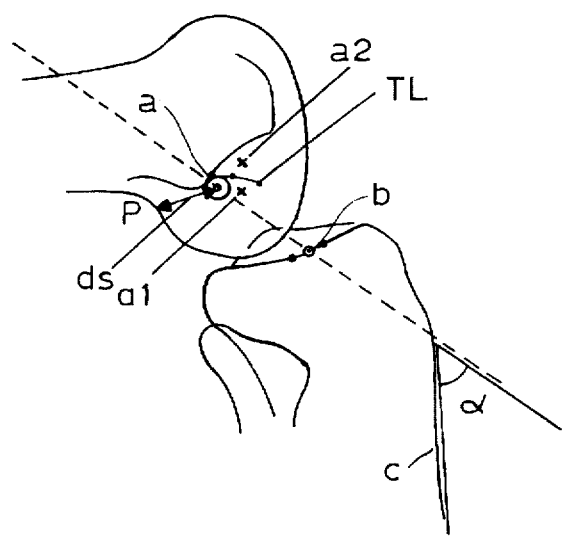
FIG. 7 is a diagrammatic side view of the knee, analogous to FIG. 4.

The method substantially comprises:

a) taking a lateral X-ray film of the extended knee, and drawing thereon three lines A, B, C parallel to the intercondylar notch roof, schematically representing the anterior, middle and posterior fibers of the ACL; the lines A, B and C are drawn parallel to the notch roof—clearly appearing as a lighter region on the X-ray film—since the ACL is parallel to said notch roof with the knee in extension, and extending these lines up to their crossing points T1, T2, T3 respectively, with the tibial plateau (FIG. 6a);

b) taking a lateral X-ray film of the knee at 90° of flexion; the 90° position can be adjusted by using a template;

c) superposing the film of the knee at 90° of flexion obtained from step b) to the film of the knee in extension obtained from step a) (FIG. 6a) by superposing the tibial contours as accurately as possible, and transferring on said overlying film of the knee at 90° of flexion a first position of points T1, T2, T3 already marked on the underlying film of FIG. 6a and seen by transparency, referencing them as T1fl, T2fl and T3fl (FIG. 6b);

d) pivoting said superposed films relative to one another, in order to now superpose the femoral axis and condylar shape as accurately as possible, and transferring on said overlying film of the knee at 90° of flexion a second position of the points T1, T2, T3 seen by transparency, referencing them as T1ext, T2ext and T3ext (FIG. 6c);

e) on the so obtained film of FIG. 6c of the knee at 90° of flexion, on which the points T1fl, T2fl and T3fl, and T1ext, T2ext and T3ext respectively, have been transferred, drawing three lines C1, C2 and C3 connecting T1ext to T1fl, T2ext to T2fl and T3ext to T3fl, respectively, and drawing three lines P1, P2 and P3 perpendicular to the center of line C1, C2 and C3, respectively (FIG. 6d);

f) determining the intersection points I1, I2 and I3 between the lines A, B and C, and lines P1, P2 and P3 (FIG. 6e); by construction, every point located on P1 will stay equidistant from T1ext and T1fl, and same is true for P2 in relation with T2ext, T2fl, and P3 in relation with T3ext, T3fl, and the line defined by connecting I1, I2 and I3 corresponds to the so called transition line described on an experimental basis by other authors; by construction, every femoral point located posterior to the transition line (such as "a1" in FIG. 7) will move away from the corresponding tibial point during extension, and every point located anterior to said transition line (such as "a2" in FIG. 7) will move in opposite direction;

g) determining the femoral target point "a" (FIG. 7); assuming the surgeon plans to create a 10 mm tunnel, point "a" which lies substantially 5 mm posterior to the transition line (TL), and 4-5 mm distal to the notch roof, as will be explained hereafter;

h) carefully measuring the distance "ds" between the point "a" and the posterior aspect of the femoral condyles (corrected according to the X-ray magnification factor);

i) drawing a line intersecting femoral target point "a" and tibial target point "b" (which corresponds to point T2 hereabove), and measuring the angle α this line makes with the anterior tibial crest or diaphysis "c".

When taking the X-ray films or radiographies, the radiologist should be careful, firstly to perfectly superpose the femoral condyles, and secondly to adjust the tibial rotation to allow perfect superposition of the tibial contours both in flexion and-extension (the peroneal head position provides a useful anatomical mark as an index of rotation).

I will refer now more particularly to the determination of target point "a" at the step g) hereabove.

As already explained, the transition line TL is the locus of isometric points. Accordingly, the target point would be determined on the transition line, the tunnel, and thus the graft substitute, would be centered on said line, and part of the graft fibers would be located posterior, and the other would be located anterior relative to said transition line. Since the graft fibers are substantially non-extensible, the extent of movement of the knee joint would be limited.

To avoid this problem, the target point "a" is actually determined so that the tunnel and the graft are tangent to the transition line. Accordingly, said target point is thus determined to be distant from the transition line TL by about half the diameter of the tunnel, as in step g) hereabove.

I will now describe the operative technique using the aiming instrument of the invention, based on the determination made by the above referenced preoperative, radiological technique.

For performing this operative technique, the patient is placed supine on the table; the leg is free, but the knee can be held in flexion during the operation placing the foot on a foot rest fixed beforehand; the foot rest position is accurately adjusted using the same 90° template as for making the preoperative X-rays; the procedure is customarily performed with regard to the arthroscopic approach, preparation of intra-articular graft insertion sites, graft harvesting, and the like.

Figure 8C:
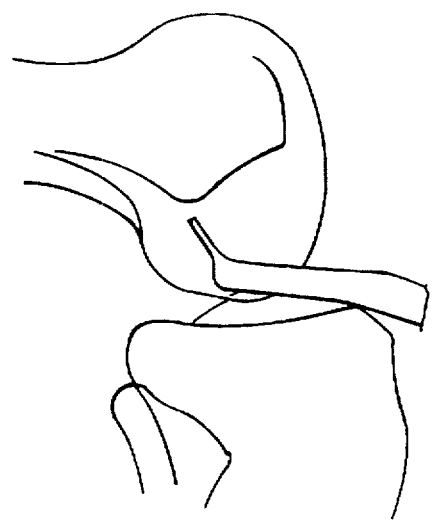
FIGS. 8a to 8c represent X-ray films of the knee, during the operative procedure.
Figure 8A:
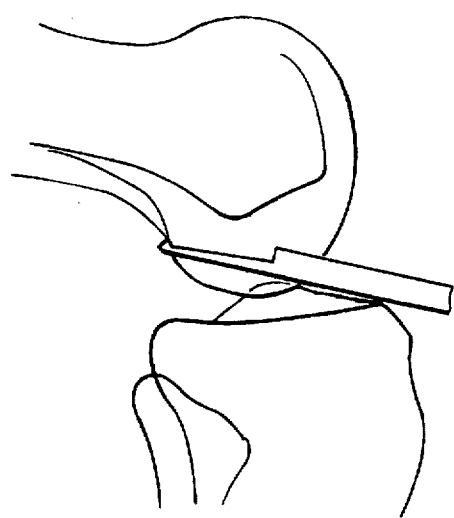
Figure 8B:
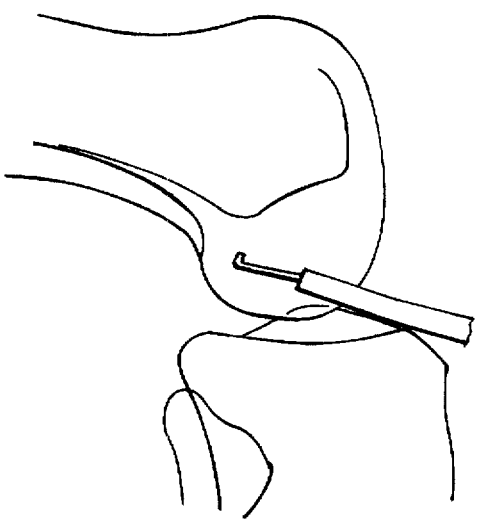

The technique proceeds as follows:

j) palpating the posterior border of the lateral femoral condyle with an ordinary arthroscopic hook 10 (FIG. 8a);

k) the hook 10 is then drawn out by the exact distance "ds" measured on the X-ray film, and a mark is made in the bone, at the junction of the roof and the lateral wall of the notch (FIG. 8b), which mark coincides with the femoral target point "a" the tip of the aiming instrument 1 is then inserted or stuck into the bone at this precise point, through an ordinary anteromedial arthroscopic approach (FIG. 8c);

m) the aiming instrument 1 is then adjusted by pivotment around the stuck tip in the frontal plane (arthroscopic adjustment) so that the instrument cuts the intercondylar space exactly in the center. In practice, the frontal adjustment is correct when the instrument arm lies in the gap between both tibial eminences. The surgeon pivots the instrument 1 to palpate the tibial plateau with the edge 6 or 7 (FIGS. 1 and 2). So doing, and possibly with the help of anatomic marks, he can rather easily locate the cavity of the interspinal space of the tibia. The orientation in the frontal plane (orientation according to FIG. 5) is obtained when, on palpation, the edge 6 or 7 comes in contact with the bottom of said spinal cavity. In the sagittal plane a goniometer is held along the anterior tibial crest, whose one branch indicates the angle α measured on the preoperative X-ray; the member 4 for aligning and guiding, or barrel of the instrument is brought parallel to this branch and firmly held in this position (FIG. 4); when the instrument is so oriented, the axis X—X thereof intersects by construction the tibial target point "b";

n) a 2.5 mm K wire is inserted in the barrel 4, and through the tibia, so that the axis thereof coincides with the axis X—X of the instrument;

o) the K wire is then inserted through the femur, the aiming instrument is removed, and the K wire overdrilled with a cannulated drill of a chosen diameter, for drilling the tibial tunnel and then the blind femoral tunnel;

p) the graft is then inserted through the tunnel, and secured to the bone according to the surgeon's own technique.

Obviously, the invention is not limited to the embodiments shown and described, which are only exemplary.

I claim:

1. A surgical instrument for aligning and guiding a piercing tool creating a tunnel through a tibia associated with a knee joint, the tunnel having an axis aligned with two predefined points of the knee joint, the knee joint having an associated intra-articulary space, the instrument comprising:

a first member for insertion into the intra-articulary space of the knee joint, the first member including a tip disposed at its distal end for locating the instrument relative to a first one of said predefined points, the first predefined point being disposed in a region located between the condyles of a femur associated with the knee joint;

means for positioning the instrument relative to a second one of said predefined points;

a second member disposed in line with said first member along the axis of the tunnel to be pierced, the second member being adapted to receive and guide the piercing tool; and, an arm connecting the first and the second members; with the axis of the tunnel to be pierced and wherein said tip is pointed towards said distal with the axis of the tunnel to be pierced and wherein said tip is pointed towards said distal end of said instrument.

2. An instrument as defined in claim 1 wherein said positioning means comprises a terminal edge of the first member, the terminal edge being located at the junction of said arm and said first member.

3. An instrument as defined in claim 2 wherein the terminal edge comprises a boss.

4. An instrument as defined in claim 1 further comprising a handle coupled to the second member for manipulating the instrument, the handle being centered on said axis.

5. An instrument as defined in claim 4 wherein the handle includes an axis located in a plane of the arm.

* * * * *

UNITED STATES PATENT AND TRADEMARK OFFICE
CERTIFICATE OF CORRECTION

PATENT NO. : 5,743,909
DATED : April 28, 1998
INVENTOR(S) : Collette

It is certified that error appears in the above-indentified patent and that said Letters Patent is hereby corrected as shown below:

Col. 8, line 14: After "... target point "a", but before "the" please insert a paragraph break and the label -- I) -- (as shown in the attached copy of the patent application, page 20).

Col. 9, lines 6-9: Please delete "with the axis of the tunnel to be pierced and wherein said tip is pointed towards said distal with the axis of the tunnel to be pierced and wherein said tip is pointed towards said distal end of said instrument." and replace with -- wherein said tip provided at said distal end of the first member is aligned with the axis of the tunnel to be pierced and wherein said tip is pointed towards said distal end of said instrument. --

Signed and Sealed this

Fourteenth Day of July, 1998

Attest:

*Attesting Officer*

BRUCE LEHMAN

*Commissioner of Patents and Trademarks*